United States Patent [19]
Bonjour et al.

[11] Patent Number: 6,149,930
[45] Date of Patent: Nov. 21, 2000

[54] METHOD OF PREPARING FUNGICIDAL COMPOSITION EMULSIONS

[75] Inventors: Anaide Bonjour; Gerardo D. Blanco; Carlos H. Canoura, all of Montevideo, Uruguay; Stuart D. Graham, Manchester, United Kingdom; Roger E. Smith, Wilmington, Del.

[73] Assignee: Avecia Inc., Wilmington, Del.

[21] Appl. No.: 09/332,684

[22] Filed: Jun. 14, 1999

Related U.S. Application Data

[62] Division of application No. 08/970,829, Nov. 14, 1997, Pat. No. 5,912,004, which is a continuation of application No. 08/410,435, Mar. 23, 1995, abandoned.

[51] Int. Cl.[7] ................................................. A01N 25/02
[52] U.S. Cl. .......................... 424/405; 424/406; 424/407; 424/410; 514/367
[58] Field of Search ................................... 424/405–406, 424/407, 410, 417; 514/367

[56] References Cited

U.S. PATENT DOCUMENTS

| | | | |
|---|---|---|---|
| 4,839,373 | 6/1989 | Ito et al. | 514/367 |
| 4,866,081 | 9/1989 | Ito et al. | 514/367 |
| 5,013,747 | 5/1991 | Katayama et al. | 514/367 |
| 5,129,946 | 7/1992 | Evans | 106/18.3 |

FOREIGN PATENT DOCUMENTS

| | | |
|---|---|---|
| 6-040819 | 2/1994 | Japan . |
| 2054587 A1 | 8/1994 | Spain . |

*Primary Examiner*—Neil S. Levy
*Attorney, Agent, or Firm*—Akin, Gump, Strauss, Hauer & Feld, L.L.P.

[57] ABSTRACT

A fungicidal composition the form of an aqueous emulsion is formed from 3-iodo-2-propynyl-N-butylcarbamate (IPBC), 2-(thiocyanomethylthio)benzothiazole (TCMTB), polyoxyethylene triglyceride, polyalkylene glycol ether, xanthan gum and dipropylene glycol. The composition is formed by adding a molten blend of polyoxyethylene triglyceride to a blend of IPBC and TCMTB, and then adding thereto a solution of xanthan gum in dipropylene glycol and water. The composition is particularly suited for the preservation of wet blue hides as obtained in the leather industry, and may also be used in the preservation of organic coatings delivered from aqueous media.

20 Claims, No Drawings

METHOD OF PREPARING FUNGICIDAL COMPOSITION EMULSIONS

CROSS-REFERENCE TO RELATED APPLICATIONS

This application is a division of application Ser. No. 08/970,829, filed Nov. 14, 1997, now U.S. Pat. No. 5,912,004, which is a continuation of application Ser. No. 08/410,435, filed Mar. 23, 1995, (abandoned).

FIELD OF THE INVENTION

The present invention relates generally to a fungicidal composition and, more particularly, to a fungicidal emulsion comprising 2-(thiocyanomethylthio)benzothiazole and 3-iodo-2-propynyl-N-butylcarbamate.

BACKGROUND OF THE INVENTION

The manufacture of leather from raw hides is a multi-step process. Cattle hides are initially obtained from a slaughterhouse, and from there taken to a tannery for processing into leather. The typical stages in this multistep process are: trimming and fleshing, soaking, hairing, liming, pickling, tanning, dyeing and finishing.

In a first step of a typical tanning process, the hides are placed into a drum which contains an acidic aqueous solution, also know as the tanning liquor. This step may be referred to as a first tanning stage. After an appropriate length of time in this tanning liquor, a basic (high pH) solution is added to the liquor in order to neutralize the acidity of the acidic aqueous solution. Then, during what is called the second tanning stage, more chemicals are added to the drum. The chemicals used in the second tanning stage may impart a bluish tinge to the hides, and thus hides that have been treated through the second tanning stage may be referred to as "wet blue hides." From the second tanning stage, the wet blue hides can be either stored for further processing or placed in a dyeing bath and then undergo further finishing.

Microbial attack of the hides can occur at many stages of the leather forming process. For example, before or immediately after being taken from a slaughterhouse, the hides may be treated with salt, which acts as a preservative while the hides are stored in the slaughterhouse, during transportation to the tannery, and during storage in the tannery. The salt must be substantially removed prior to the tanning process, and this is typically done, in part, by soaking the hides in water, optionally with agitation. Bacterial attack can occur during this soaking stage.

Also, while the hides are in, or being transported after, the second tanning stage, the hides are subject to fungal attack. For example, it is not uncommon for wet blue hides to be transported across long distances from a tannery to a leather processor, where the wet blue hides will be finished. Fugal attack of the wet blue hides is thus a concern for leather manufacturers.

Biocides are used to protect the hides from bacteria, mold and fungi. Fungal attack on leather results in unattractive black dots or other discoloration on the hides, which are very difficult to remove and/or may spoil the finish leather or wet blue hides. *Aspergillus niger* is a typical fungus which may attack leather. ASTM D 4576-86 (reapproved 1991) describes a test method for evaluating the mold growth resistance of blue stock leather, also called wet blue hides, that have been treated with fungicide.

U.S. Pat. No. 4,866,081 discloses that the combination of 2-(thiocyanomethylthio)-benzothiazole and 3-iodo-2-propynyl-N-carbamate, is particularly useful as a microbicidal preservative to prevent deterioration of raw materials such as dyes, pastes, lumber, leather, textiles and pulp caused by microorganisms.

There remains a need in the art for biocidal formulations which may be effectively added to water-based systems, including tanning baths for leather manufacture and aqueous inks and other coatings.

SUMMARY OF THE INVENTION

The invention provides a fungicidal composition comprising a stable aqueous emulsion. The stable aqueous emulsion comprises a blend of 2-(thiocyanomethylthio) benzothiazole (TCMTB) and 3-iodo-2-propynyl-N-butylcarbamate (IPBC) in a TCMTB:IPBC weight ratio of about 0.03:1 to about 30:1 and a total weight percentage of TCMTB and IPBC, based on the total weight of emulsion, of about 10 to about 30 percent. The emulsion further comprises at least one non-ionic surfactant and at least one thickening agent.

The invention further provides for a method for preparing the stable emulsion described above, which comprises the steps: (a) forming a homogeneous blend comprising 3-iodo-2-propynyl-N-butylcarbamate and 2-(thiocyanomethylthio) benzothiazole; (b) forming nonionic surfactant in a liquid state; and (c) adding the surfactant of step (b) to the blend of step (a) with stirring. In a further step (d), a homogeneous blend comprising water and thickening agent is formed; and the blend of step (d) is added to the product of step (c) with stirring to form a homogeneous emulsion.

The invention also provides for a method for imparting fungi-resistance to hides. The method comprises placing hides in an aqueous solution useful for at least one of pickling hides or forming wet blue hides, and adding the fungicidal emulsion described above to the aqueous solution either before or after addition of the hides.

Another aspect of the invention is a method for imparting fungi-resistance to an organic coating delivered from an aqueous medium. The method comprises adding the fungicidal emulsion described above to an aqueous medium which contains the coating material suspended or dissolved therein.

DETAILED DESCRIPTION OF THE PREFERRED EMBODIMENTS

The present invention is directed to a fungicidal composition comprising TCMTB and IPBC. The composition is designed to be efficacious as a fungicide when added to leather during the tanning process, and is particularly useful as a fungicide present during the preparation of wet blue hides. The inventive composition is also useful in the preservation of organic coatings, such as paint.

As used herein, TCMTB refers to 2-(thiocyanomethylthio)benzothiazole, CAS No. 21564-17-0. IPBC refers to 3-iodo-2-propynyl-N-butylcarbamate, CAS No. 55406-53-6. TCMTB is a commercial product, and can be obtained from, for example, Albright & Wilson as Tolcide® C60. TCMTB may also be obtained from Buckman Laboratories International, Inc., Memphis, Tenn. as Busan® 30. IPBC is likewise a commercial product, and can be obtained from, for example, Troy Chemical Corporation as Troysan® Polyphase® AF1.

While the combination of TCMTB and IPBC has been reported to be a useful fungicide, the prior art does not suggest how that combination may be incorporated into aqueous based systems such as used in leather manufacture. For example, leather processing, as described previously, relies on soaking hides in aqueous solutions. Also, aqueous inks and coatings are steadily replacing organic solvent-based inks and coatings due to environmental and health concerns. Both TCMTB and IPBC are organic materials, and not expected to be appreciably water soluble materials. As described herein, developing a composition comprising TCMTB and IPBC, where that composition can be added to tanning liquor and impart fungicidal properties thereto, has been a significant challenge.

The composition of the invention is an aqueous emulsion comprising TCMTB and IPBC. The water is preferably potable, with an approximately neutral pH of about 5 to about 9, and preferably has a calcium carbonate level of less than about 25 ppm.

The weight ratio of TCMTB:IPBC in the emulsion of the invention may vary depending on the microorganism(s) being targeted, and the material to which the emulsion is being applied. Typically, a weight ratio of TCMTB:IPBC of about 0.03:1 to about 30:1 will be satisfactory. One skilled in the art can readily determine, without undue experimentation, an appropriate weight ratio for a specific application. Preferably, the weight ratio of TCMTB:IPBC ranges from about 0.4:1 to about 7:1, more preferably, from about 0.8:1 to about 1.8:1. A TCMTB:IPBC weight ratio of about 1.3:1 has been found to be particularly effective in an emulsified composition intended for the preservation of wet blue hides and organic coatings, and such a composition may be prepared according to the methodology disclosed herein.

The concentration of the total of the TCMTB and IPEC in the inventive emulsion may be about 10 to about 30 weight percent, and more preferably is about 15 to about 20 weight percent. A concentration of about 17 weight percent is particularly suitable for an emulsion intended for the preservation of wet blue hides or organic coatings, wherein the TCMTB contributes about 9.6 weight percent and the IPBC contributes about 7.4 weight percent.

At least one non-ionic surfactant is necessarily present in the inventive emulsion. Exemplary, suitable non-ionic surfactants include, without limitation, polyoxyethylene triglyceride, polyoxyethylene-(100)-stearate, polyoxyethylene-(30)-nonylphenol and polyalkylene glycol ether. The numbers within the parentheses refer to the number of ethylene oxide derived units in the surfactant. Polyoxyethylene triglyceride is commercially available from, e.g., ICI Americas Inc., Wilmington Del., as Atlox® 1285. Polyalkylene glycol ether is commercially available from, e.g., ICI Americas Inc., Wilmington Del., as Atlas G-5000®. In a preferred embodiment of the invention, the non-ionic surfactant is a blend of polyoxyethylene triglyceride and polyalkylene glycol ether.

As well known in the art, nonionic surfactants may be characterized by their hydrophilic/lipophilic balance, also known as an HLB value. Preferred nonionic surfactants, including blends thereof, for the inventive emulsion have an HLB value of about 15.9 to about 16.9. Polyalkylene glycol ether, as available from ICI Americas Inc. (Wilmington, Del.) as Atlas G-5000®, has an HLB value of 16.9. Polyethyleneoxide triglyceride, as available from ICI Americas Inc. (Wilmington, Del.), as Atlox 1285®, has an HLB value of 14.4. Thus, in a preferred embodiment, the emulsion prepared using a blend of Atlas G-5000® and Atlox 1285® contains more Atlas G-5000® than Atlox 1285®, so that the surfactant blend will have an HLB value within the preferred range. According to a preferred embodiment, the emulsion has a polyoxyethylene triglyceride:polyalkylene glycol ether ratio of about 1:9.

The surfactant(s) chosen for combination with TCMTB and IPBC must provide a stable oil-in-water emulsion, and preferably provide compatibility with the solutions used in a tanning process or other aqueous-based system in need of fungi resistance. By "compatibility" with the solutions used in a tanning process, it is meant that the addition of the composition of the invention to such solutions provides a stable, homogeneous mixture.

The total non-ionic surfactant in the composition may range from about 8 to about 12 weight percent, with a concentration of about 10 weight percent being preferred. In a preferred embodiment, the non-ionic surfactants is a blend of polyoxyethylene triglyceride and polyalkylene glycol ether, where the blend constitutes about 10 weight percent of the composition of the invention, and the polyoxyethylene triglyceride is preferably present at about 1 weight percent while the polyalkylene glycol ether is present at about 9 weight percent, in the inventive emulsion.

A final necessary ingredient of the inventive emulsion is a thickening agent. Thickening agents, as is well known in the art, are materials which may be added to water in small quantity to provide an increase in the viscosity of the water/solution. Xanthan gum, an example of a polysaccharide thickening agent, is a preferred thickening agent according to the invention.

The thickening agent may be present in the emulsion at a concentration of about 0.05 to about 0.2 weight percent, with a preferred concentration of about 0.1 weight percent when the thickening agent is xanthan gum.

The fungicidal emulsion of the invention may additionally contain at least one glycol, where glycol as used herein refers to a polyhydric organic compound having exactly two hydroxyl (—OH) groups. There are several advantages to the presence of glycol in the emulsion. For example, if the thickening agent is a solid, it may be more easily and effectively combined with the other ingredients in the emulsion if the thickening agent has been wetted with glycol and/or water prior to its addition to the emulsion. By the term wetting it is meant that the solid thickening agent has been mixed with solvent, preferably including glycol, so that the thickening agent dissolves, or at least becomes homogeneously distributed throughout, and in intimate contact with, the solvent. When xanthan gum is wetted with glycol, a ratio of gum to glycol of about 1:10 has been found suitable, and the resulting wetted gum has the appearance of a gel. Either more or less glycol may be used to wet the xanthan gum, depending on the preferences of the user.

Another advantage to including glycol in the inventive emulsion is that glycol may encourage intimate contact between the leather and the active ingredients of the emulsion, i.e., the TCMTB and IPBC. In other words, penetration of the fungicidal composition in leather may be improved by including glycol within the emulsion composition. Improved penetration may be due, in part, to an enhancement in the compatibility of the fungicide-containing emulsion with the tanning liquor, caused by the presence of glycol. The glycol may also contribute to the long-term stability of the fungicide-containing emulsion.

The glycol that may be used to prepare the inventive emulsion preferably has exactly two hydroxyl groups and at least about 6 carbon atoms. Thus, ethylene glycol, propylene glycol and ethyldiglycol (a.k.a. ethanol, 2-(2-ethoxyethoxy), are preferably not present in the inventive emulsion to any substantial extent. Ethylene glycol is preferably not present because it has been found responsible for imparting a brittle appearance to the surface of finished leather. Propylene glycol may discourage the emulsified TCMTB/IPBC from forming a non-homogeneous composition with tanning liquor, and thus it is not a preferred glycol. Dipropylene glycol is exemplary of a preferred glycol according to the invention.

A concentration of glycol of up to about 25 weight percent may be present in the inventive composition. It will be appreciated that the addition of glycol to the formulation should take into consideration the glycol that may be present due to its co-formulation with either or both of TCMTB and IPBC. That is, TCMTB and IPBC are commonly obtained as solutions, where the solvent may comprise glycol. For example, when the IPBC is obtained as a 40 weight percent solution from Troy Chemical known as Troysan Polyphase AF-1, that product contains about 15 weight percent dipropylene glycol.

For best results, the ingredients are preferably not simply combined and agitated, as that approach will not provide a stable emulsion. According to the preferred method, TCMTB and IPBC are combined in a first reaction vessel, and blended by agitation to provide a homogeneous blend.

In a second reaction vessel, the surfactant, including blends thereof, is made into a liquid state. Liquifying the surfactant will typically involve heating the surfactant to a molten state, as many surfactants are solid at room temperature. Dissolution of the surfactant in a solvent may be an alternative viable option for liquification. When the surfactant is a mixture of polyoxyethylene triglyceride and polyalkylene glycol ether, the two surfactants are preferably combined and heated to about 60° C., with stirring, to provide a homogeneous blend.

According to the preferred embodiment, a third reaction vessel is used to wet the thickening agent. When the thickening agent is xanthan gum, the gum may be treated with dipropylene glycol while maintaining gentle stirring, and then water is added to the gum/dipropylene glycol mixture with additional stirring. The dipropylene glycol helps to wet, or "open up" the xanthan gum in the water.

To provide the emulsified product, the surfactant is added to the blend of TCMTB and IPBC. In a preferred embodiment, the surfactant will be a blend of polyoxyethylene triglyceride and polyalkylene glycol ether at about 60° C., and the addition of said surfactant to the TCMTB/IPBC blend will produce a mixture having a temperature of about 40° C. After achieving the mixture of TCMTB/IPBC and surfactant, the thickening agent is added to the mixture along with water and any glycol which may have been used to encourage wetting of the thickening agent. Stirring continues until an emulsion forms. Thereafter, additional water and/or glycol may be added to the emulsion.

The present invention also provides a method for inhibiting the growth of fungi on wet blue hides. According to the inventive method, wet blue hides are contacted with the composition of the invention as described above, in an amount effective to inhibit the growth of the fungi.

The concentration of the fungicidal composition that should be contacted with the hides is highly dependent on the process conditions used in the tanning process. The desired degree of protection from fungal attack will also influence the amount of the TCMTB/IPBC emulsion contacted with the hides. When a high level of fungal protection for wet blue hides is desired, the inventive emulsion should be added at a concentration of about 0.05 to about 0.2 weight percent, based on the weight of the hides. That is, about 1 part hides should be treated with about 0.0005 to about 0.002 parts emulsion. The inventive emulsion may also be added at earlier stages in the leather-making process, for example, during the pickling or tanning stages.

As there is tremendous variation in the procedures used by various tanneries to tan hides, one skilled in the art may need to conduct some experimentation to determine an optimal level of the inventive emulsion to add to the baths which treat the hides. However, the following general procedure may be used as a guide, and is based on a typical pickling/tanning process.

| OPERA-TION | FLOAT % w/w | TEMP. ° C. | CHEMICAL | DOSE % | RUNNING TIME MIN |
|---|---|---|---|---|---|
| Add | 60 | 30 | Salt | 8.0 | 10 |
| Add | | 30 | Formic Acid | 0.3 | 20 |
| Add | 10 | | Sulphuric Acid | 1.1 | 120 |
| Add | | | Sodium Formate | 0.7 | 15 |
| Add | | | Chrom. Sulphate | 4.0 | 60 |
| Add | | | Soda Ash | 1.0 | |
| Add | | | FUNGICIDE(*) | x.x | 360 |
| Adjust pH 3.8–4.1 | | | | | 60–120 |
| Rise Temp. to: | | 45 | | | 60 |

(*)FUNGICIDE = Composition of Inventive Example 1

The emulsion of the invention may also be used to protect organic coatings from fungi-induced degradation. For example, the inventive emulsion may be added to water-based inks and paints, so that upon application to a substrate and drying to remove water and other volatile components, the remaining coating displays resistance to mold.

The amount of the emulsion of the invention desirably added to an aqueous ink or paint will naturally depend on the identity of the ink or paint, the environment to which the dried coating will be exposed, and the degree of protection desired. A dose of about 1 weight percent, that is, about 1 part of inventive emulsion added to about 99 parts of aqueous media, that is, the aqueous ink or paint, has been found satisfactory in acrylic and polyvinyl acetate containing paints. One can use as little as about 0.3 parts fungicidal emulsion in 100 parts aqueous media, and still obtain satisfactory results in some instances. Reducing the dose below about 0.3 parts per 100 parts aqueous media affords less protection for the coating. The addition of more fungicide to the aqueous media is typically better, that is, a higher dose generally affords a higher degree of protection for the dried coating. However, cost considerations typically limit the dose to less than about 5%. Also, at very high doses, the properties of the coating may be adversely effected by the presence of the fungicidal composition.

While the composition of the invention has been described as being particularly useful in the leather manufacturing industry, and in the manufacture of aqueous inks and paints, it should be understood that the composition may also be fungicidally efficacious when used in other contexts, such as in preventing the deterioration of various types of industrial raw materials and products, including dyes, pastes, lumber, textiles and pulp other water-based products including adhesives and cosmetics, which are subject to decay and molding caused by microorganisms such as fungi.

The invention will now be illustrated by the following non-limiting examples, which demonstrate the advantageous benefits of the present invention. In the examples, all of "parts" or "pts" and "%" are by weight unless otherwise indicated. TCMTB, which is an abbreviation for 2-(thiocyanomethylthio)benzothiazole, is available from many sources, including Bayer (Germany) under the tradename Preventol® CR, Albright & Wilson Ltd. (U.K.) under the tradename Tolcide® C, and Buckman Laboratories International, Memphis Tenn., under the tradename Busan®. IPBC, which is an abbreviation for 3-iodo-2-propynyl butyl carbamate, is available from Troy Chemical, Newark, N.J. under the tradename Troysan® Polyphase® AF1. Each supplier typically provides TCMTB or IPBC as a formulated mixture, where the amount of active ingredient in the mixture is indicated with the name. For example, Busan 30 contains 30% TCMTB and 70% other ingredients.

INVENTIVE EXAMPLE 1

A blend was prepared by combining 16 parts Tolcide® C60 and 18.5 parts Troysan® Polyphase® AF1 in a vessel equipped with a vapor extraction system, and stirring until a homogeneous blend results.

In a separate operation, 1 part of Atlox 1285 (ICI Chemicals & Polymers, U.K.) and 9 parts Atlas G-5000 (ICI Chemicals & Polymers, U.K.), which are a polyoxyethylene triglyceride and a polyalkylene glycol ether, respectively, are combined in a vessel and heated to 60° C. with stirring until a homogeneous blend results.

In yet another vessel, 0.1 parts xanthan gum (Rhodopol® XB 23, Rhone-Poulenc, France), 1.0 parts dipropylene glycol and about 27 parts water were combined and stirred until a homogeneous, fluid, translucent gel resulted. An agitation time of about 15–30 minutes was used, and the stirring was done at room temperature.

The surfactants were added to the TCMTB/IPBC solution with stirring, and the temperature of the mixture was about 40° C. After a few minutes, the xanthan gel was added to the surfactants/TCMTB/IPBC mixture, with stirring. Stirring was maintained until a homogeneous emulsion resulted. The final temperature of the emulsion was about 40° C.

The product was stable to 20 minutes centrifugation at 2250 rpm. Upon combination with acid tannery liquor, which was achieved simply by adding the emulsion to the tanning liquor with stirring, there was no separation after 24 hours.

INVENTIVE EXAMPLE 2

An emulsion was prepared according to the procedure provided in Inventive Example 1, by combining 16 parts Tolcide C60, 18.5 parts Troysan Polyphase AF1, 1 part Atlox 1285, 9 parts Atlas G-5000, 0.1 parts Rodhopol XB 23 (predissolved in 1 part dipropylene glycol) and 55.4 parts water. Aliquots of the resulting emulsion were combined with dipropylene glycol such that 100 parts emulsion were combined with either 5, 10 or 20 parts dipropylene glycol. Each of the combinations was stable by themselves, and stable when combined at a concentration of 1 in tanning liquor.

COMPARATIVE EXAMPLE 1

A blend was prepared by mixing 63 parts Busan 30 and 37 parts Troysan Polyphase AF1). The blend was unstable.

COMPARATIVE EXAMPLE 2

A blend was prepared by mixing 24 parts Tolcide C80, 39 parts Troysan Polyphase-AF1 and 37 parts water. The blend had an TCMTB/IPBC ratio of 1.3. The blend was not stable, and immediately upon formation separated into distinct phases.

COMPARATIVE EXAMPLE 3

A blend was prepared by mixing 24 parts of Busan C80, 37 parts Troysan Polyphase AF1 and 39 parts water. This blend was not stable, and immediately upon formation separated into distinct phases.

COMPARATIVE EXAMPLE 4

A blend was prepared by mixing 24 parts Busan 80, 37 parts Troysan Polyphase AF1, 4 parts polyoxyethylene triglyceride (Atlox 1285, ICI Chemicals & Polymers, U.K.), 6 parts calcium alkylaryl sulfonate (Atlox 3404 from ICI Chemicals & Polymers, U.K.) and 29 parts xylene.

The stability of the blend was evaluated by combining 1 part blend with 99 parts water, and a reasonably stable product resulted. However, the flash point of the blend was high, making it troublesome from a handling and transportation viewpoint. When evaluated at a tannery, the blend did not properly incorporate into the tanning bath.

COMPARATIVE EXAMPLE 5

A blend was prepared by mixing 12.5 parts Busan 80, 18.5 parts Troysan Polyphase AF1, 4.5 parts polyoxyethylene triglyceride, 5.5 parts calcium alkylaryl sulfonate and 59.5 parts ethyldiglycol (also known as ethanol, 2-(2-ethoxyethoxy) or diethylene glycol ethyl ether). Upon mixing with tannery liquor, bloom formation was fine, however the blend imparted an undesirable brittleness to the leather.

COMPARATIVE EXAMPLE 6

A blend was prepared according to the recipe set forth in Comparative Example 5, except that the ethyldiglycol was replaced with propylene glycol. The resulting formulation had poor stability upon being added to the tannery liquor, as noted by the formation of an oily layer on top of the tannery liquor after about 1 hour of addition of the blend thereto.

APPLICATION EXAMPLE 1

One cow hide and 5 liters of tanning liquor were obtained from a commercial tannery. The hide was drained to about 50–60% moisture, and then twelve samples, each having a known weight of about 100 grams, were cut from the hide. Two samples were placed into each of five drums, labelled A through E, where each drum additionally contained tanning liquor at 100% float, suitable for preparing wet blue hides.

Fungicide was added to each of the drums A through E, where the concentration of fungicide is indicated in TABLE I. The fungicide added to drum A was Busan® 30. The fungicide added to drums B and C was the emulsion of Inventive Example 2 to which no dipropylene glycol had been added. The fungicide added to drums D and E was the emulsion of Inventive Example 2 to which had been added 10 weight percent dipropylene glycol.

The samples were maintained in the tanning liquor for about 6 hours, and then removed from the liquor and evaluated for their resistance to mold growth according to the procedure described in ASTM Designation: D 4576-86 (Reapproved 1991). The samples were placed in the center of a labelled Petri dish, with the surface to be tested facing up. The Petri dishes were labelled A through E to correspond to the identification of the drums. In addition, a Petri dish labelled F was used, which contained only media. Petri dish F served to ensure that the inoculum was active. A few drops of *Aspergillus niger* spores in water were dropped onto each sample of wet blue hide and media. The formation of black dots, indicative of mold growth, was monitored periodically.

TABLE I

| DRUM | FUNGICIDE CONCEN- TRATION | 7 DAYS | 10 DAYS | 14 DAYS | 21 DAYS |
|---|---|---|---|---|---|
| A | 0.1 | 0.0 | 0.17 | 1.0 | 4.0 |
| B | 0.1 | 0.0 | 0.0 | 0.0 | 3.0 |
| C | 0.2 | 0.0 | 0.17 | 0.50 | 1.0 |
| D | 0.1 | 0.0 | 0.17 | 0.17 | 0.17 |
| E | 0.2 | 0.33 | 0.33 | 0.50 | 0.50 |
| F | 0.0 | 4.0 | 4.0 | 4.0 | 4.0 |

TABLE II

RATING SCALE

| Numerical Rating | % Surface Mold Growth |
|---|---|
| 0.0 | None |
| 0.5 | <12 |
| 1.0 | 25 |
| 2.0 | 50 |
| 3.0 | 75 |
| 4.0 | 100 |

APPLICATION EXAMPLE 2

Two white, aqueous-based paints were obtained from Akzo, Brazil. The binder in paint A was acrylic and the binder in paint B was polyvinyl acetate. Samples of each of the paints were combined with the emulsion prepared as described in Inventive Example 1.

Coatings from the emulsion-dosed paints were prepared on paper, and the resistance of coatings to mold attack was monitored, as described in a test method published by the U.S. government, specifically Test Method 6271.2 as appears in Fed. Test Method Std. No. 141C. Briefly, the coating was placed on a one-inch square sheet of paper, a border was drawn on the paper at a distance of 1/16 inch from the edge of the sheet, and the sheet was placed coating side up into a petri dish containing agar. An inoculum of test organism was spread across the coating and agar, and a lid placed on the dish. After 7 days, the coated paper was examined to see if any mold spots appeared within the border. "Pass" in TABLES III and IV indicates that no mold spots were observed.

As seen in TABLES III and IV, the composition prepared according to Inventive Example 1 was compared to commercially available fungicides. Densil ND contains zinc oxide, chlorothalonil, and 2,3,5,6 tetrachloro-4(methyl sulphonyl)pyridine. Densil S-25 contains 2,3,5,6 tetrachloro-4(methyl sulphonyl)pyridine. Densil P contains dithio-2,2'-bis(benzmethylamide). Each of the Densil products is available from Zeneca, Inc., Wilmington Del.

In TABLES III and IV, "C1 (Paper)" and "C2 Paint" refer to controls 1 and 2 respectively. Control 1 consisting of placing an uncoated piece of paper into the petri dish. Control 2 consisted of coating a piece of paper with the paint, without having previously added fungicide.

TABLE III

Summary of Results for Evaluation of Composition of Inventive Example 1 in Acrylic Paint

ACRYLIC PAINT - AKZO BRAZIL

| Dose (% w/w) | Inv. Ex. 1 | Densil ND | Densil S-25 | Densil P |
|---|---|---|---|---|
| C1 (Paper) | Fail | Fail | Fail | Fail |
| C2 (Paint) | Fail | Fail | Fail | Fail |
| 0.15 | Fail | Fail | Fail | Fail |
| 0.30 | Fail | Pass | Pass | Fail |
| 0.50 | Fail | Pass | Pass | Fail |
| 0.75 | Fail | Pass | Pass | Fail |
| 1.00 | Pass | Pass | Pass | Pass |
| 1.25 | Pass | Pass | Pass | Pass |
| 1.50 | Pass | Pass | Pass | Pass |

TABLE IV

Summary of Results for Evaluation of Composition of Inventive Example 1 in Polyvinyl Acetate Paint

POLYVINYL ACETATE PAINT - AKZO BRAZIL

| Dose (% w/w) | Inv. Ex. 1 | Densil ND | Densil S-25 | Densil P |
|---|---|---|---|---|
| C1 (Paper) | Fail | Fail | Fail | Fail |
| C2 (Paint) | Fail | Fail | Fail | Fail |
| 0.15 | Fail | Fail | Fail | Fail |
| 0.30 | Pass | Pass | Pass | Fail |
| 0.50 | Pass | Pass | Pass | Fail |
| 0.75 | Pass | Pass | Pass | Fail |
| 1.00 | Pass | Pass | Pass | Pass |
| 1.25 | Pass | Pass | Pass | Pass |
| 1.50 | Pass | Pass | Pass | Pass |

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

What is claimed is:

1. A method for preparing a stable, aqueous, fungicidal emulsion, consisting essentially of 2-(thiocyanomethylthio) benzothiazole (TCMTB) and 3-iodo-2-propynyl-N-butylcarbamate (IPBC) in a TCMTB:IPBC weight ratio of about 0.03:1 to about 30:1 and a total weight percentage of TCMTB and IPBC, based or the total weight of emulsion, of about 10 to about 30%; a nonionic surfactant; a thickening agent; and a glycol having at least six carbon atoms and exactly two hydroxyl groups; comprising the steps of:
   (a) forming a homogenous blend of the TCMTB and IPBC;
   (b) providing the nonionic surfactant in a liquid state;
   (c) combining the honmogenous blend of step (a) with the nonionic surfactant of step (b), with stirring, to form a combination thereof;
   (d) wetting the thickening agent with the glycol; and
   (e) combining the wetted thickening agent of step (d), with the combination of step (c), with stirring, to form a homogenous emulsion.

2. The method according to claim 1, wherein said TCMTB:IPBC weight ratio is about 0.4:1 to about 7:1.

3. The method according to claim 1 wherein said TCMTB:IPBC weight ratio is about 0.8:1 to about 1.8:1.

4. The method according to claim 1 wherein said total weight percentage is about 15 to about 20 percent.

5. The method according to claim 1 wherein the emulsion contains about 9.6 weight percent TCMTB and about 7.4 weight percent IPBC.

6. The method according to claim 1 wherein said nonionic surfactant is present in said emulsion at a concentration of about 8 to about 12 weight percent, based on the total weight of said emulsion.

7. The method according to claim 1 wherein said nonionic surfactant has a hydrophilic/lipophilic balance (HLB) of about 15.9 to about 16.9.

8. The method according to claim 1 wherein said nonionic surfactant is selected from the group consisting of polyoxyethylene triglyceride, polyoxyethylene-(100)-stearate, polyoxyethylene-(30)-nonylphenol and polyalkylene glycol ether.

9. The method according to claim 1 wherein said nonionic surfactant is a blend of polyoxyethylene triglyceride and polyalkylene glycol ether.

10. The method according to claim 9 wherein said blend has a weight ratio of polyoxyethylene triglyceride:polyalkylene glycol ether of about 1:9.

11. The method according to claim 1 wherein said thickening agent is present at a concentration of about 0.05 to about 0.2 weight percent in said emulsion.

12. The method according to claim 1 wherein said thickening agent is a polysaccharide.

13. The method according to claim 1 wherein said thickening agent is xanthan gum.

14. The method according to claim 1 wherein the nonionic surfactant of step (b) is a blend of polyoxyethylene triglyceride and polyalkylene glycol ether in a weight ratio of polyoxyethylene triglyceride:polyalkylene glycol ether of about 1:9, and wherein providing the liquid state is accomplished by heating the blend of step (b) to a temperature of about 60° C.

15. The method according to claim 1 wherein said glycol is dipropylene glycol.

16. The method according to claim 1 wherein said glycol is present in said emulsion at a concentration of not more than about 25 weight percent of said emulsion.

17. The method according to claim 1 wherein said glycol is present in said emulsion at a concentration of about 5 to about 10 weight percent of said emulsion.

18. The method according to claim 1 wherein said emulsion consisting essentially of about 9.6% TCMTB, about 7.4% IPBC, about 1% polyoxyethylene triglyceride, about 9% polyalkylene glycol ether, about 0.1% xanthan gum and at least about 4% dipropylene glycol, where each percentage is weight percent based on the total weight of emulsion.

19. The method according to claim 1 wherein the wetted thickening agent of step (d) comprises xanthan gum and dipropylene glycol in a weight ratio of xanthan gum:dipropylene glycol of about 1:10.

20. The method according to claim 1 wherein the homogeneous blend of step (a) has a TCMTB:IPBC weight ratio of about 0.8:1 to about 1.8:1 and a total weight percentage, based on the total weight of emulsion, of about 15 to about 20.

* * * * *